(12) United States Patent
Peck

(10) Patent No.: US 7,051,574 B2
(45) Date of Patent: *May 30, 2006

(54) FLOW CELL HUMIDITY SENSOR SYSTEM

(75) Inventor: Bill J. Peck, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/990,941

(22) Filed: Nov. 16, 2004

(65) Prior Publication Data
US 2005/0130210 A1 Jun. 16, 2005

Related U.S. Application Data

(63) Continuation of application No. 10/017,336, filed on Dec. 13, 2001, now Pat. No. 6,838,888.

(51) Int. Cl.
G01N 19/10 (2006.01)
G01N 27/22 (2006.01)
G01R 27/26 (2006.01)

(52) U.S. Cl. ............... 73/29.01; 73/335.04; 73/29.05; 324/689

(58) Field of Classification Search ............... 73/29.01, 73/335.03, 335.04, 335.05, 29.05; 324/689
See application file for complete search history.

(56) References Cited

U.S. PATENT DOCUMENTS

| 6,119,506 A | 9/2000 | Gibson et al. |
| 6,242,266 B1 | 6/2001 | Schleifer et al. ............ 436/518 |
| 6,413,783 B1 | 7/2002 | Wohlstadter et al. |
| 2003/0008413 A1 | 1/2003 | Kim et al. |

Primary Examiner—Daniel S. Larkin

(57) ABSTRACT

A system for monitoring water concentration in gaseous sample is disclosed. It is readily applicable in the synthesis of biopolymer arrays/microarrays involving the use of water-sensitive reagents. A flow cell is provided in which a capacitance sensor is placed separate from a production or synthesis environment. Sample and dry gas may be provided to the flow cell via conduits and valves or a manifold system. Dry gas, such as $N_2$, is used to dry the sensor or simply to maintain it in a dried condition. The same gas may be used to drive an optional venturi pump to draw sample for measurement into the cell from the synthesis environment.

15 Claims, 4 Drawing Sheets

FLOW CELL HUMIDITY SENSOR SYSTEM

THIS APPLICATION is a continuation of application Ser. No. 10/017,336, FILED Dec. 13, 2001, now U.S. Pat. No. 6,838,888, UNDER 35 U.S.C. 120, THE ENTIRETY OF WHICH IS INCOPORATED HERE IN BY REFERENCE.

FIELD OF THE INVENTION

This invention relates to sensor use, particularly capacitance-type humidity sensors (i.e., dew point sensors). A system for drying or maintaining sensor dryness in a flow cell is disclosed. It is advantageously used in synthesis procedures requiring anhydrous or near-anhydrous environments.

BACKGROUND OF THE INVENTION

It is often important to maintain low-humidity environments in various synthesis or manufacturing processes. For instance, successful in-situ synthesis of biopolymer "biochips" or arrays/micorarrays may require an anhydrous, or substantially humidity-free environment, e.g., where the biopolymer ligands of the array are "grown" in situ using chemical synthesis protocols that produce the ligands through stepwise addition of activated monomers. Water concentrations in such an environment sometimes need to be as low as 1 PPMv (e.g., in laying-down protein or DNA microarrays).

In order to maintain a production environment in an anhydrous or near-anydrous state—adjusting conditions or terminating activity if environmental conditions pass beyond acceptable limits—accurate monitoring is required. Typically, in response to sensor readings indicating higher humidity levels, the production environment is "blown-out" with dry gas, such as $N_2$ gas. This purges unwanted moisture from the synthesis area.

To maintain extremely low water vapor concentrations, measurements are typically taken using a capacitance-type sensor. In a capacitance or dew point sensor, water vapor absorbed or desorbed by a porous layer alters the layer's capacitance. This alteration is measured using adjacent conductive members in order to provide a humidity reading.

In such a sensor, water is absorbed much more quickly than it is desorbed.

Accordingly, it has been appreciated that quicker response time may be achieved in taking humidity measurements using a dry sensor than one that has already been saturated. A dewpoint meter produced by Xentaur (Medford, NY: Model-XPDM), capitalizes on this feature by isolating a sensor in a region filled with dessicant until it is withdrawn therefrom and exposed in another region to sample gas.

The present invention, likewise, uses an isolated sensor approach.

However, an improved manner of sensor drying and/or maintaining a sensor in a dry state is taught herein. Instead of requiring a complex apparatus including multiple chambers and perishable dessicants like the referenced system, a more elegant system is described. In addition to such advantages as increased reliability, ease of operation and maintenance, and cost or space savings, variations of the inventive system offer further possible advantages that may be apparent to those skilled in the art.

SUMMARY OF THE INVENTION

The present invention includes methods and apparatus for making minimum-response time water concentration measurements for gas samples used in various environments with a discrete sample flow cell. The sample cell includes a capacitance sensor therein. Sample and dry gas, such as $N_2$, is provided to the cell via conduits and valves or a manifold system. The dry gas is used to dry the sensor or simply to maintain it in a dried condition. The same gas may be used to drive a pump, preferably a venturi pump, to draw sample into the sample cell for measurement.

The inventive system is advantageously used in synthesis procedures involving water-sensitive reactants. Methodology associated therewith, such as the routine for running the flow cell humidity sensor system as particularly described below, and complete manufacturing systems including printing systems and biological material form part of the present invention. Arrays and other products produced using the inventive system may also form part of the invention.

BRIEF DESCRIPTION OF THE DRAWINGS

Each of the following figures provide examples diagrammatically illustrating aspects of the present invention. Of these.

DETAILED DESCRIPTION OF THE INVENTION

Before the present invention is described in detail, it is to be understood that this invention is not limited to the particular variations set forth and may, of course, vary. Various changes may be made to the invention described and equivalents may be substituted without departing from the true spirit and scope of the invention. In addition, many modifications may be made to adapt a particular situation, material, composition of matter, process, process step or steps to the objective, spirit and scope of the present invention. All such modifications are intended to be within the scope of the claims made herein. Furthermore, where a range of values is provided, it is understood that every intervening value, between the upper and lower limit of that range and any other stated or intervening value in that stated range is encompassed within the invention. That the upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications, patents and patent applications mentioned herein are incorporated herein in their entirety. The referenced items are provided solely for their disclosure prior to the filing date of the present application. Nothing herein is to be construed as an admission that the present invention is not entitled to antedate such material by virtue of prior invention.

It is also noted that as used herein and in the appended claims, the singular forms "a," "and," and "the" include plural referents unless the context clearly dictates otherwise. In the claims, the terms "first," "second" and so forth are to be interpreted merely as ordinal designations, they shall not be limiting in themselves. Further, the use of exclusive terminology such as "solely," "only" and the like in connection with the recitation of any claim element is contemplated. Also, it is contemplated that any element indicated to be optional herein may be specifically excluded from a given claim by way of a "negative" limitation. Finally, it is contemplated that any optional feature of the inventive variation(s) described herein may be set forth and claimed independently or in combination with any one or more of the features described herein.

Figure 1:
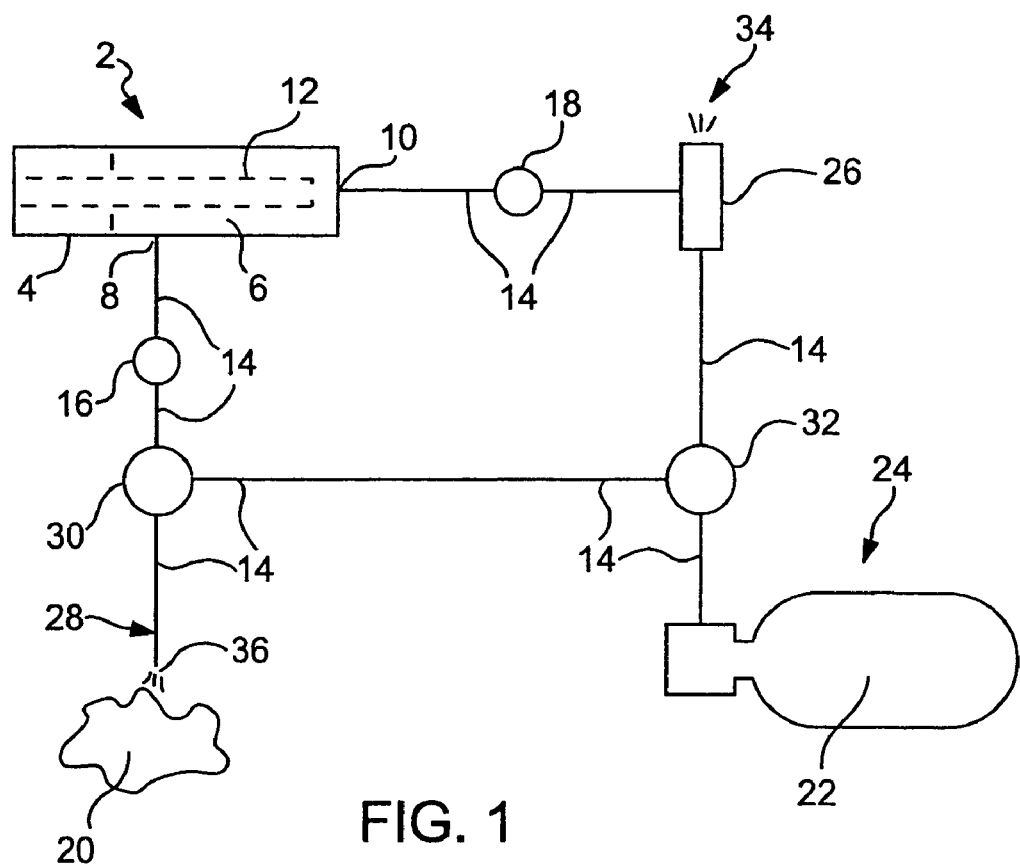
FIG. 1 shows an overview of the inventive system.

Turning now to FIG. 1, elements of the present invention are shown. A flow-cell (2) is provided by a body (4) defining a chamber interior (6). The flow cell includes a first port (8) and a second port (10). Other ports as may be convenient can be included as well, so long as the flow-cell (2) and a capacitance type sensor probe (12) located therein comprise a sealed system when desired, that is discrete or apart from the environment from which sample is acquired. A suitable capacitance sensor (12) is produced by Xentaur Corporation (Medford, N.Y.: Model No. XTR-100 or, more preferably, Model No. XTR-100P).

It is preferably operated in a typical fashion, where changes in capacitance across adjacent conductive members is correlated to the moisture content of a gaseous sample by way of appropriate hardware/software, such as an XDT-PM/C transmitting unit available through Xentaur Corporation.

Flow cell body (4) preferably comprises stainless steel. Its interior wall(s) are preferably electropolished to minimize water adsorption within chamber (6) introduced by sample gas. Chamber (6) is preferably cylindrical. So-shaped, with the first and second ports located orthogonally as shown and sensor (12) fixed coaxially, optimal mixing of gas may be achieved within the chamber around a sensor (12). The size or volume of the flow cell chamber may be between about 100 to 500 ml. The dimensions will typically be constrained by mounting the apparatus in a working environment and ensuring the incoming flow is as homogenous as possible as it passes over the sensing element.

Lines or conduit members (14) may be used to connect the various components of the inventive system. However connected, a first valve (16) and a second valve (18) may be provided in fluid communication to flow cell (2). Preferably, the valves are two-way solenoid valves. Suitable valves are produced by KIP Inc. (Farmington, Conn.: Model No. 241043—configured as a two way valve). Together, they serve to open and close the flow cell, alternately exposing it to sample gas (20) or dry gas (22) from a dry gas source or supply (24).

Source (24) may comprise a regulated $N_2$ tank. Other gasses (especially any other dry inert gas or a noble gasses) or source types may be used. What is important is that gas supply (24) be able to deliver anhydrous gas to sensor (12). The purpose of this is to either maintain sensor (12) in a dehydrated state or to provide an environment in which the sensor will desorb water it contains and become dehydrated.

The inventive system may also include a pump (26). The pump preferably comprises a venturi-type device. Optionally, it is run by dry gas supply (24). Other types of pumps or vacuum devices may be used instead. For instance, any common industrial-type vacuum supply may be used. Pump (26) is preferably set to draw sample through flow cell (2) via a siphon (28).

The inventive system may also include third and fourth valves (30) and (32), respectively. These too may be solenoid valves. These valves are preferably configured for 3-way operation. Suitable valves are produced by KIP Inc. (Farmington, Conn.: Model No. 241043—configured as a three-way valve).

In combination, the hardware thus far described may be used to perform various tasks. However, as will be apparent, not all of such hardware is necessary to perform each function. Accordingly, various subcombinations of the inventive features performing any of the stated functions may equally be regarded as forming an aspect of the invention as well as a complete system able to perform all the functions described.

In this regard, it is noted that first and second valves (16) and (18), may be closed-off to isolate flow-cell (2) from high humidity levels during servicing of any system plumbing or prolonged delay in use. This state of valve closure defines a "shut-down" mode. In this mode, humidity levels in the flow-cell chamber are maintained substantially constant.

Figure 2A:
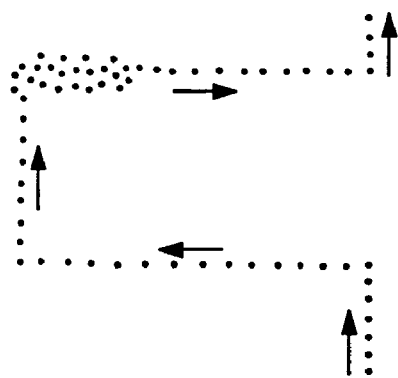
FIG. 2A shows drying flow within a system configuration like that in FIG. 1.
Figure 2B:
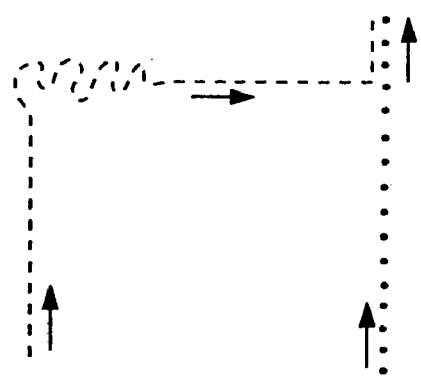
FIG. 2B shows sampling flow within a system configuration like that in FIG. 1.

During operation, "dry-down" and "sampling" modes are typically employed. FIG. 2A shows an example of the former, while FIG. 2B shows an example of the latter.

In dry-down mode, the valves are set so that dry gas is passed through flow cell (2) by sensor (12). As configured, $N_2$ gas will also flow out the venturi pump as exhaust. The desired dry gas flow depicted by a dotted path—which is set by valves (16), (18), (30) and (32)—enters flow cell (2) by port (8), passes over and around sensor (12) causing it to desorb moisture and exits flow cell (2) by port (10). Moisture-laden gas may then exit the inventive system via pump exhaust port (34). Desired flow rates for such a procedure are between about 0.25 and 2 CFM, set by appropriate pressure.

Running under such conditions, it has been observed that even a completely saturated sensor (i.e. one registering greater than 1000 PPMv) can be adequately dried to a resolution limited steady state measurement (i.e. one registering $\leq 1$ PPMv) between about 20,000 and 30,000 seconds. With an adequately dry sensor (12), upon exposure to moisture-laden gas an accurate reading may be obtained in about 400 seconds. This feature is in comparison to a period of several days required in taking a reading by a sensor simply exposed to sample from a target environment.

In sampling mode, gas from source (24) running at a higher pressure/flow rate than in dry-down mode is diverted through venturi (26) by valve (32). In FIG. 2B, this activity is again indicated by a dotted path. Flow rates of dry gas to venturi (26) are preferably between about 1 and 2 CFM depending on the venturi, driven by pressure set to between about 60 and 80 PSI. This generates a vacuum between about 10 and 20 mmHg. By virtue of the setup of valves (16), (18) and (30), the vacuum generated draws sample gas (20) by siphon (28) through flow cell (2) as indicated in FIG. 2B by dashed lines. Both dry gas and sample gas exit venturi exhaust port (34) as shown.

Using a dry gas/venturi setup is preferred in acquiring sample since it alleviates danger of contaminating sensor (12) by hydrated gas that might invade the sensor chamber (6) before a steady state is reached. This being said, dry-down and sampling procedures may be accomplished otherwise. For instance, any sort of vacuum pump may be used to draw sample gas through flow cell (2). Further, dry gas may be passed through the flow cell directly without intervening plumbing routing it to achieve multiple functions. Still, the configuration shown in FIG. 1 and the flow paths shown in FIGS. 2A and 2B comprise most preferred aspects of the invention.

The inventive system may be set to alternate between sampling and dry-down modes for taking successive humidity readings. In instances where sampling soon after a first sample is taken is not desired or required, however, the inventive system may be set to remain in dry-down mode until sensor (12) is sufficiently dry, whereupon flow-cell (2) is isolated by valves (16) and (18) as in the shutdown mode to conserve dry gas supplies. Such variability in system usage is preferably implemented with appropriate electronic hardware under software control. Suitable controllers for use in any manner of control of the aforementioned steps are produced by Keithley Instruments or National Instruments.

In preparation for sampling, a sample siphon end (36) is preferably placed in close relation to the target environment that is separate from flow cell (2). As noted above, the invention is advantageously used in any number of biopolymer array production procedures involving the use of water-sensitive reactants, e.g., activated nucleotides or amino acids for the preparation of nucleic acids or polypeptides, respectively. It may be most preferred to use features of the invention in connection with a protein or DNA array/microarray production environment in which an ink-jet printhead deposits material onto a substrate. Siphon end (36) is preferably placed within about 1 and 10 mm of the print site or a reaction/binding site. The siphon end may be associated with the printhead to maintain this spacing and move with the printhead to successive sample sites. Alternately, siphon end (36) may remain stationary as long as it is downwind of gas flow within the production environment from the reaction/printing site.

Siphon end (36) is preferably relatively small in order to minimize air disturbances in the sampling environment. It may have an outer diameter of between about 0.125 and 0.25 inch with an inner diameter between about 0.0625 and 0.125. A typical volume of sample it will obtain may be between about 5 liters/minute and 20 liters/minute.

A system advantageously used in connection with the present invention is described in U.S. patent application Ser. No. 10/017,107, titled "Printhead Fluid Supply System,") filed on even date herewith. Further chemical array printing system features advantageously used in connection with the present system are described in the references cited therein, including U.S. patent application Ser. No. 09/150,504 titled, "Method and Apparatus for Making Nucleic Acid Arrays;" U.S. patent application Ser. No. 09/300,589 titled, "Method of Performing Array-Based Hybridization Assays Using Thermal Inkjet Deposition of Sample Fluids;" U.S. patent application Ser. No. 09/846,474 titled "Error Detection In Chemical Array Fabrication"; and U.S. Pat. Nos. 6,242,266 and 6,180,351. Other components of array printing systems which may be adapted for use with the present invention include U.S. Pat. Nos. 4,877,745; 5,338,688; 5,474,796; 5,449,754; 5,658,802 and 5,700,637.

Arrays produced with the invention will be used with one or more additional components necessary such as sample preparation reagents, buffers, labels or the like. Some or all of these components may be provided in packaged combination with a set of instructions, possibly associated with a package insert or the package itself. Biochip or array devices may be used in any number of analyte detection assays including differential gene expression assays, gene identification assays, nucleotide sequencing assays, and the like. Further uses of arrays made according to the present invention are also described in the above cited references.

The arrays produced by the subject methods find use in a variety applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; WO 95/21265; WO 96/31622; WO 97/10365; WO 97/27317; EP 373 203; and EP 785 280; the disclosures of which are herein incorporated by reference.

In gene expression analysis with microarrays, an array of "probe" nucleic acids is contacted with a nucleic acid sample of interest. Contact is carried out under hybridization conditions and unbound nucleic acid is then removed. The resultant pattern of hybridized nucleic acid provides information regarding the genetic profile of the sample tested. Gene expression analysis finds use in a variety of applications, including: the identification of novel expression of genes, the correlation of gene expression to a particular phenotype, screening for disease predisposition, identifying the effect of a particular agent on cellular gene expression, such as in toxicity testing; among other applications.

In certain embodiments, the subject methods of analyte detection, as described above, include a step of transmitting data from at least one of the detecting and deriving steps, as described above, to a remote location. The data may be raw data (such as fluorescence intensity readings for each feature in one or more color channels) or may be processed data such as obtained by rejecting a reading for a feature which is below a predetermined threshold and/or forming conclusions based on the pattern read from the array (such as whether or not a particular target sequence may have been present in the sample). By "remote location" is meant a location other than the location at which the array is present and hybridization occur. For example, a remote location could be another location (e.g. office, lab, etc.) in the same city, another location in a different city, another location in a different state, another location in a different country, etc. The data may be transmitted or otherwise forwarded to the remote location for further evaluation and/or use. Any convenient telecommunications means may be employed for transmitting the data, e.g., facsimile, modem, internet, etc. When one item is indicated as being "remote" from another, this is referenced that the two items are at least in different buildings, and may be at least one mile, ten miles, or at least one hundred miles apart. "Communicating" information references transmitting data representing that information as signals (such as electrical or optical) over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

Following receipt by a user of an array made by an apparatus or method of the present invention, as described above, the array will typically be exposed to a sample (for example, a fluorescently labeled polynucleotide or protein containing sample) and the array then read. Reading of the array may be accomplished by illuminating the array and reading the location and intensity of resulting fluorescence at each feature of the array. For example, a scanner may be used for this purpose which is similar to the GENEARRAY scanner manufactured by Agilent Technologies, Palo Alto, Calif. Other suitable apparatus and methods are described in U.S. patent applications: Ser. No. 09/846125 "Reading Multi-Featured Arrays" by Dorsel et al.; and Ser. No. 09/430214 "Interrogating Multi-Featured Arrays" by Dorsel et al. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,251,685, U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample, or whether or not a pattern indicates a particular condition of an organism from which the sample came). The results of the reading (processed or not) may be forwarded (such as by communication) to a remote location if desired, and received there for further use (such as further processing).

EXAMPLE

Figure 3A:
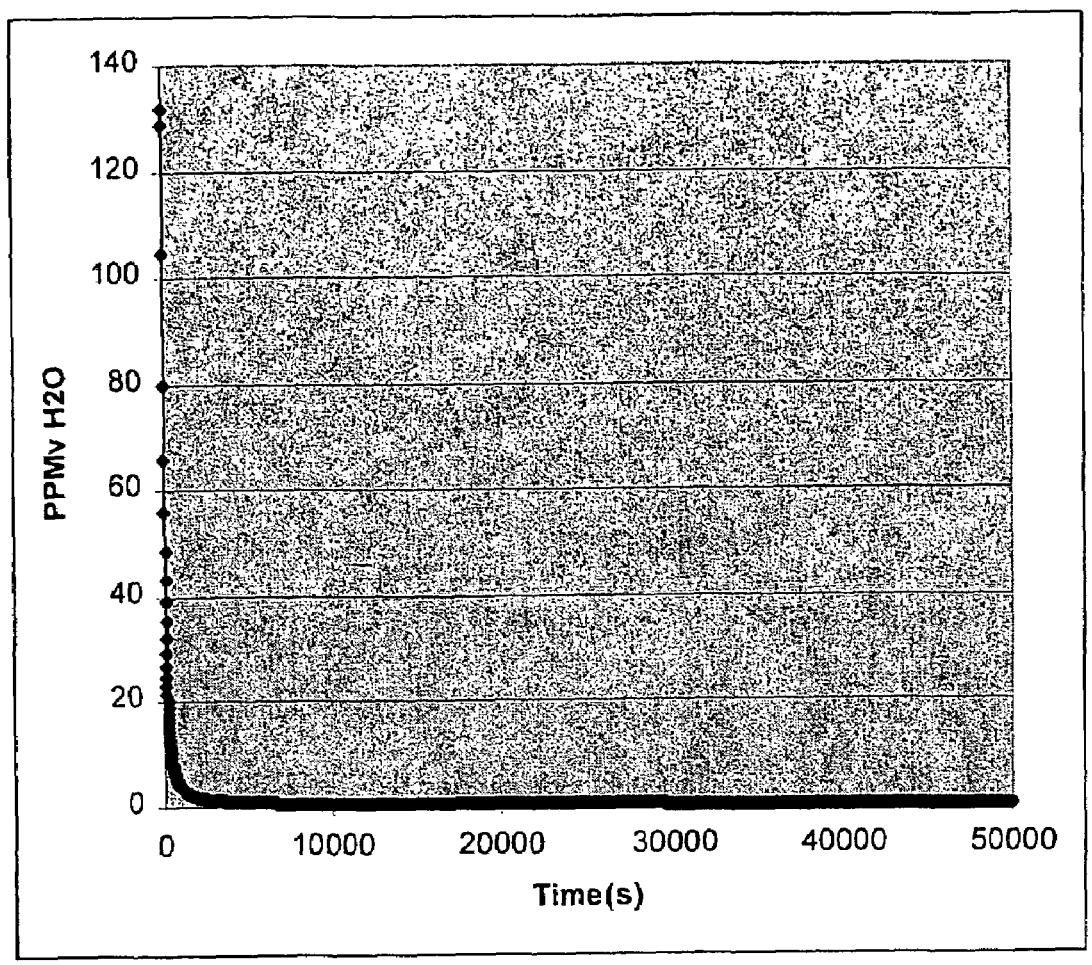
FIGS. 3A–3C each show a graphical representation of data characterizing actual performance of a system according to the present invention.
Figure 3B:
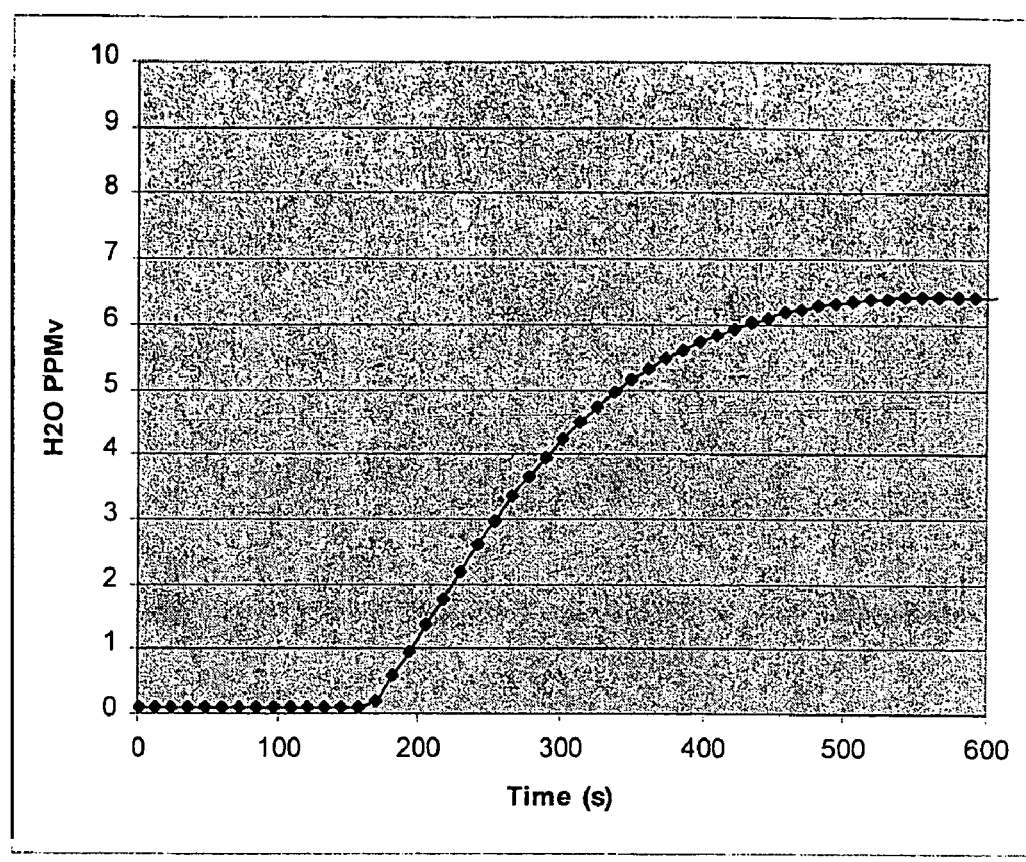
Figure 3C:
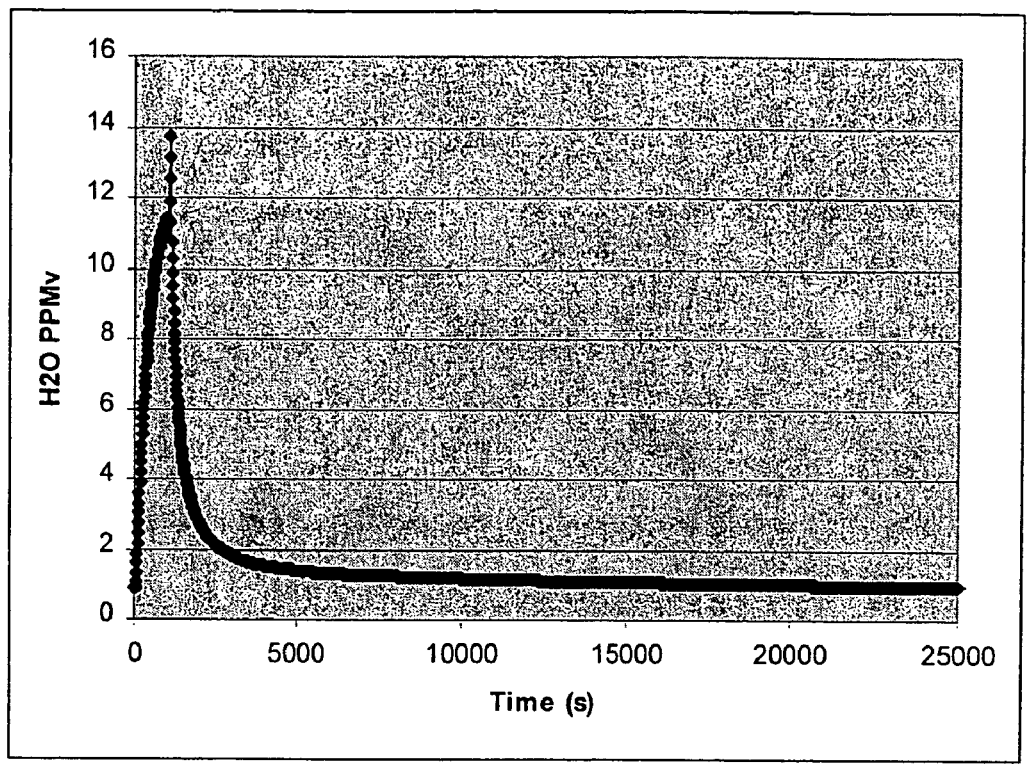

The graphical data shown in FIGS. 3A–3C characterize actual performance with an embodiment of the present invention. FIG. 3A depicts dry-down of a capacitance sensor in a flowcell (2) under $N_2$ purge. The sensor requires only a matter of hours to reach resolution limited/sub-1 PPMv levels of $H_2O$. FIG. 3B depicts sensor (12) response to a step change of 6.5 PPMv from house gas reading 0.093 PPMv. The sensor achieves a resolution limited steady state after about 400 seconds. FIG. 3C depicts the response of an initially dry sensor that has been wetted to greater than 12 PPMv and then dried according to the present invention. The entire process takes roughly 20,000 seconds to achieve a resolution limited steady state value.

The invention claimed is:

1. An array production system comprising: an environment for holding a chemical array substrate, and a capacitance measurement system comprising,
    a body defining a chamber having first and second ports, said chamber containing a capacitance sensor probe,
    first and second valves, said first valve in communication with said first port and said second valve in communication with said second port, and
    a dry gas source,
    wherein a sampling conduit provides fluid communication through said first port between said chamber and said environment, and
    wherein said valves am positioned to allow dry gas to flow through said chamber in one state to dehydrate said sensor, and a gaseous sample from said environment to flow through said chamber in another state.

2. The system of claim 1, further comprising a vacuum pump in fluid communication with said chamber to draw sample into said chamber.

3. The system of claim 2, wherein said vacuum pump comprises a venturi device.

4. The system of claim 3, wherein said venturi device is driven by said dry gas source.

5. The system of claim 1, wherein said ports are oriented orthogonally along said body.

6. The system of claim 2 wherein said first and second valves are two-way valves and said system further comprises third and fourth three-way valves, said third and fourth valves in communication with each other, said third valve also in communication with said first valve and said sampling conduit, said fourth valve also in communication with said dry gas source and said pump, said second valve also in communication with said pump, wherein said pump comprises a venturi device.

7. A method of capacitance measurement for determining water content of a gaseous sample from an environment for holding a chemical array substrate comprising:
    flowing dry gas over a capacitance sensor provided in a body defining a chamber apart from said environment so said sensor desorbs water,
    terminating said flowing of dry gas, and
    flowing said gaseous sample from said environment over said sensor to measure water content of said gaseous sample.

8. The method of claim 7, further comprising isolating said capacitance sensor in the presence of dry gas to maintain a low water content.

9. The method of claim 7, wherein negative pressure from a venturi pump draws said gaseous sample from a sample site through a flow-cell containing said sensor.

10. The method of claim 7, wherein a biopolymer is synthesized on the substrate in the environment.

11. The method according to claim 10, wherein said biopolymer is a polypeptide or nucleic acid.

12. The method of claim 10, wherein said substrate comprises an array of biomonomers or biopolymers and the substrate is contacted with a fluid provided by the chamber.

13. A capacitance measurement system for determining water content of a gaseous sample comprising:
- a body defining a chamber containing a capacitance sensor probe, a dry gas source, and a venturi device,
- wherein said system is configured so said venturi device produces a negative pressure within said chamber in one state,
- wherein said system is configured so said dry gas source provides a flow of dry gas within said chamber to pass over said sensor probe to dehydrate it in another state,
- wherein said chamber is apart from an environment for holding an array substrate, from which environment a gaseous sample is to be sampled for moisture by said capacitance sensor probe, and
- wherein a sampling conduit provides fluid communication for said gaseous sample through said-tint a port between said chamber and the environment.

14. The system of claim 13, wherein said system is configured to draw said gaseous sample gas Into said chamber by said negative pressure.

15. The system of claim 13, wherein said venturi device is driven by said dry gas.

* * * * *